US012114415B2

(12) United States Patent
 Aoki (10) Patent No.: US 12,114,415 B2
(45) Date of Patent: Oct. 8, 2024

(54) CIRCULAR ACCELERATOR

(71) Applicant: Hitachi High-Tech Corporation, Tokyo (JP)

(72) Inventor: Takamichi Aoki, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 17/892,311

(22) Filed: Aug. 22, 2022

(65) Prior Publication Data

US 2022/0408541 A1 Dec. 22, 2022

Related U.S. Application Data

(62) Division of application No. 16/341,072, filed as application No. PCT/JP2017/011906 on Mar. 24, 2017, now Pat. No. 11,457,523.

(51) Int. Cl.
 *H05H 7/04* (2006.01)
 *A61N 5/10* (2006.01)
 (Continued)

(52) U.S. Cl.
 CPC ............... *H05H 7/04* (2013.01); *A61N 5/103* (2013.01); *A61N 5/1077* (2013.01); *H01F 7/202* (2013.01);
 (Continued)

(58) Field of Classification Search
 CPC .. A61N 5/103–1084; A61N 2005/1085–1098; H05H 5/00–08;
 (Continued)

(56) References Cited

U.S. PATENT DOCUMENTS 6,236,043 B1    5/2001  Tadokoro et al.
2007/0170994 A1  7/2007  Peggs et al.
 (Continued)

FOREIGN PATENT DOCUMENTS

CN    102651942 A    8/2012
CN    104813750 A    1/2014
 (Continued)

OTHER PUBLICATIONS

International Search Report of PCT/JP2017/011906 dated Jun. 13, 2017.
(Continued)

*Primary Examiner* — Thaddeus B Cox
(74) *Attorney, Agent, or Firm* — MATTINGLY & MALUR, PC (57) ABSTRACT

Provided is a variable energy and miniaturized accelerator. It is impossible to change the energy of the extraction beam in the related cyclotron or to miniaturize an accelerator in the related synchrotron. The accelerator includes a pair of magnets which form a magnetic field therebetween; an ion source which injects ions between the magnets; an acceleration electrode which accelerates the ions; and a beam extraction path which extracts the ions to the outside. A plurality of ring-shaped beam closed orbits formed by the pair of magnets, in which the ions of different energies respectively circulate, are aggregated on one side. The frequency of the radiofrequency electric field fed to the ions by the acceleration electrode is modulated by the beam closed orbits.

5 Claims, 10 Drawing Sheets

(51) Int. Cl.
*H01F 7/20* (2006.01)
*H05H 7/08* (2006.01)
*H05H 13/00* (2006.01)
*H05H 13/02* (2006.01)
*H05H 15/00* (2006.01)

(52) U.S. Cl.
CPC ............ *H05H 7/08* (2013.01); *H05H 13/005* (2013.01); *H05H 13/02* (2013.01); *H05H 15/00* (2013.01); *A61N 2005/1087* (2013.01); *A61N 2005/1097* (2013.01)

(58) Field of Classification Search
CPC ................. H05H 7/00–10; H05H 7/22; H05H 9/00–048; H05H 11/00–04; H05H 13/00–10; H05H 15/00; H05H 2277/00–1405
See application file for complete search history.

(56) References Cited

U.S. PATENT DOCUMENTS

2009/0236545 A1 9/2009 Timmer
2012/0217903 A1 8/2012 Tanaka et al.
2014/0014851 A1 1/2014 Asaba

FOREIGN PATENT DOCUMENTS

| | | |
|---|---|---|
| JP | 2014-020800 A | 2/2014 |
| JP | 2014-160613 A | 9/2014 |
| JP | 2014-186939 A | 10/2014 |
| WO | 2013/072397 A1 | 5/2013 |
| WO | 2014052708 A2 | 4/2014 |
| WO | 2016/092621 A1 | 6/2016 |
| WO | 2016092623 A1 | 6/2016 |

OTHER PUBLICATIONS

Chinese Office Action dated Sep. 2, 2020, issued in corresponding Chinese Patent Application No. 201780068779.2.
Partial supplementary European search report dated Oct. 7, 2020, issued in corresponding European Patent Application No. 17902515.0.
Takayama et al., "Racetrack-shape fixed field induction accelerator for giant cluster ions", Physical Review Special Topics—Accelerators and Beams, vol. 18, No. 5, published May 8, 2015.
Roberts et al., "The microtron as a high-energy, high current particle accelerator", Annals of Physics, New York, NY, US, vol. 4, pp. 115-165, Jun. 1, 1958.
Extended European Search Report received in corresponding European Application No. 23179177.3 dated Jan. 30, 2024.
Clark, D. J., "A Microtron Cyclotron The "Slipatron"", Proceedings of the 14th International Conference on Cyclotrons and their Applications, Jan. 1, 1996, pp. 618-620.

CIRCULAR ACCELERATOR

TECHNICAL FIELD

The present invention relates to an accelerator accelerating heavy ions, such as protons or carbon ions.

BACKGROUND ART

High-energy nuclear beams used in particle therapy, physical experiments, and the like are generated using an accelerator. Examples of accelerators that obtain a beam having kinetic energy of about 200 MeV per nucleus include a cyclotron described in Patent Literature 1 and Patent Literature 2, a synchrotron described in Patent Literature 3, and a variable energy accelerator described in Patent Literature 4. A characteristic of the cyclotron is to accelerate the beam circulating in a static magnetic field in a radiofrequency electric field. As accelerated, the beam increases a radius of curvature of its orbit, moves to an orbit on an outer side, and is extracted after reaching the highest energy. Therefore, the energy of the extracted beam is fixed. The synchrotron temporally changes the magnetic field of a magnet that bends the beam and frequency of a radiofrequency electric field that accelerates the beam, such that the beam circulates in a fixed orbit. Therefore, it is also possible to extract the beam before reaching the maximum energy in design, and the extraction energy can be controlled. The variable energy accelerator is characterized in that, while accelerating a beam circulating in a magnetic field which is the same as in the cyclotron in a radiofrequency electric field, the beam orbit deviates in one direction along with acceleration.

PRIOR ART LITERATURE

Patent Literature

PTL 1: JP-A-2014-160613
PTL 2: JP-A-2014-020800
PTL 3: JP-A-2014-186939
PTL 4: WO2016-092621

SUMMARY OF INVENTION

Technical Problem

The cyclotron described in Patent Literature 1 or the variable energy accelerator described in Patent Literature 4 makes an average magnetic field on the orbit proportional to a relativistic γ factor of the beam, such that time of the circulation is fixed regardless of the energy. A magnetic field distribution having this property is referred to as an isochronous magnetic field. By the way, under the isochronous magnetic field, by modulating the magnetic field along the orbit, beam stability in a direction perpendicular to the inside of an orbital plane and the orbital plane is ensured.

Thus, in order to achieve both isochronism and beam stability, a maximum portion (Hill) and a minimum portion (Valley) are required. A non-uniform magnetic field of this distribution can be formed by making a distance (gap) between opposing magnetic poles of the main magnet narrow in the Hill area and wider in the Valley area. However, a difference between the Hill magnetic field and the Valley magnetic field has a limit that is saturation magnetic flux density of a magnetic pole material which is a ferromagnetic material. That is, the difference between the Hill magnetic field and the Valley magnetic field is limited to approximately 2 T.

Meanwhile, when miniaturizing the accelerator, it is necessary to increase the main magnetic field to reduce a bending radius of the beam orbit. However, the main magnetic field and the difference between the Hill magnetic field and the Valley magnetic field described above are in a proportional relationship, and the limit described above is a factor for determining an actual size of the accelerator. Therefore, particularly in the variable energy accelerator, there is a problem in that the difference in the magnetic field required for deviating and aggregating the beam orbit in one direction along with acceleration becomes an obstacle, which makes it difficult to miniaturize the size.

Solution to Problem

In order to solve the problems, for example, a configuration described in claims is adopted.

Though the invention includes a plurality of means that solve the above problems, one example thereof includes a pair of magnets which form a magnetic field therebetween, an ion source which injects ions between the magnets, an acceleration electrode which accelerates the ions, and a beam extraction path which extracts the ions to the outside. A plurality of ring-shaped beam closed orbits formed by the pair of magnets, in which the ions of different energies respectively circulate, are aggregated on one side. The frequency of the radiofrequency electric field fed to the ions by the acceleration electrode is modulated by the beam closed orbits.

Advantageous Effect

According to the invention, a miniaturized and variable energy accelerator is provided.

DESCRIPTION OF EMBODIMENTS

Embodiment 1

Figure 1:
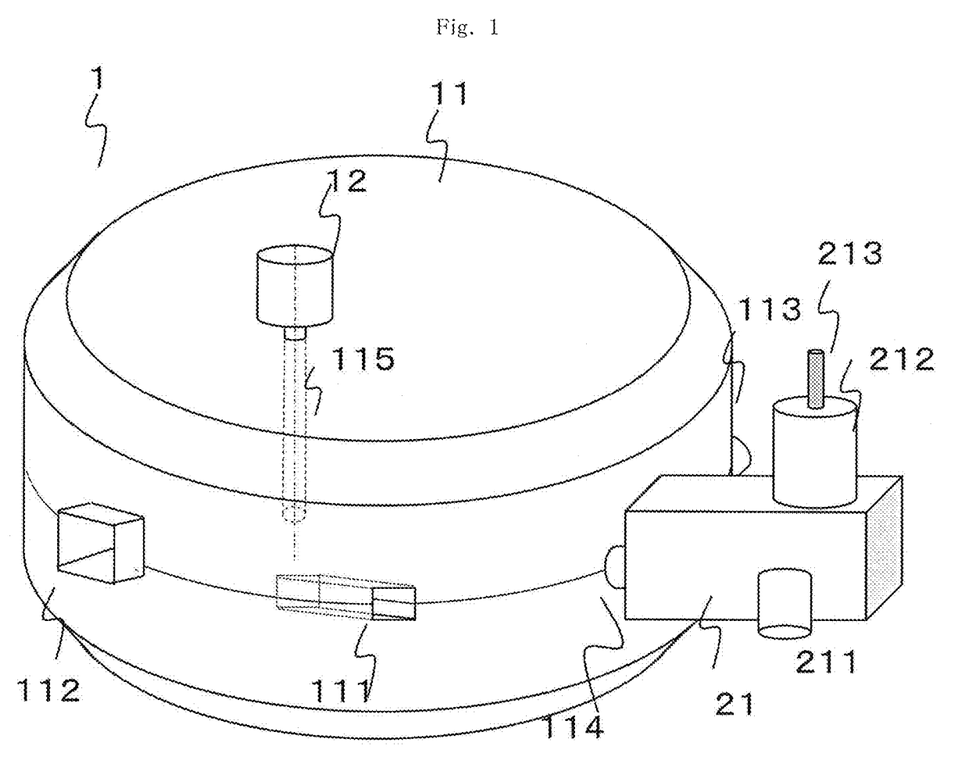
FIG. 1 is an overall outline of an accelerator 1 in an embodiment.

An accelerator according to a first embodiment, which is a preferred embodiment of the invention, will be described below with reference to FIGS. 1 to 4. The accelerator 1 in the embodiment is a frequency modulation type variable energy accelerator having variable energy property. The accelerator 1 is a circular accelerator that accelerates protons circulating in a temporally fixed magnetic field by a radiofrequency electric field. The appearance thereof is illustrated in FIG. 1. The accelerator 1 excites a main magnetic field in a region through which a beam passes (hereinafter, referred to as a beam passing region) by a vertically dividable magnet 11, and the inside of the beam passing region is evacuated. A plurality of through holes are formed in the magnet 11, and an extraction beam through hole 111 which extracts the accelerated beam, drawing ports 112 and 113 which draws out coil on the inside to the outside, and a radiofrequency power input through hole 114 are provided on a connection plane of upper and lower magnetic poles. A radiofrequency cavity 21 is installed through the radiofrequency power input through hole 114. As will be described later, an acceleration dee electrode portion and a rotating variable capacitance capacitor 212 are installed in the radiofrequency cavity 21. An ion source 12 is installed at a position deviated from the center of an upper portion of the magnet 11 and at a different position in the radial direction. The beam is injected to the inside of the accelerator 1 through the beam injection through hole 115.

Figure 2:
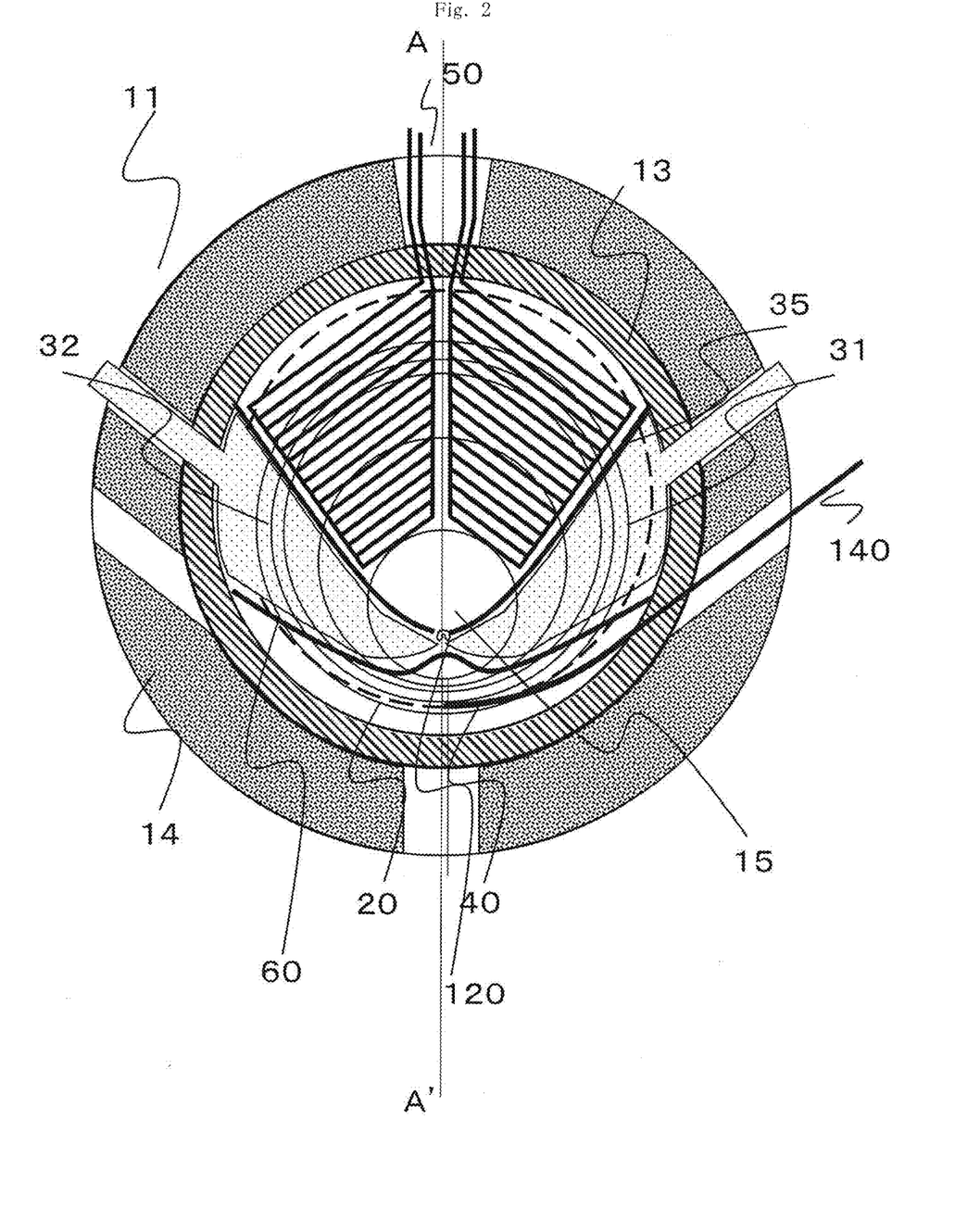
FIG. 2 is an internal device arrangement diagram of the accelerator 1 in the embodiment.

Next, an internal structure of the accelerator will be described with reference to FIG. 2. The inside of the magnet 11 includes a cylindrical beam passing region 20 formed by a cylindrical inner wall, and an annular coil 13 is installed along the inner wall. When a current is passed through the coil 13, the magnet 11 is magnetized and excites the magnetic field in a predetermined distribution described later in the beam passing region 20. A magnetic pole 15 is vertically opposed inside the coil 13 so as to form a vertical boundary of the beam passing region 20, and an outer side of the coil 13 includes a cylindrical return yoke 14. The beam is accelerated while circulating in the beam passing region 20. Energy of the extraction beam is from a minimum of 70 MeV to a maximum of 235 MeV, and a circulating frequency of the beam is 59 to 76 MHz. The magnetic field formed by the magnetic pole 15 is uniform along the orbit of the beam and creates a distribution such that the magnetic field decreases as the energy increases. That is, a magnetic field is formed so as to decrease the magnetic field on an outer side of the radial direction. Under such a magnetic field, betatron oscillation occurs stably in an orbital plane of the beam and in a direction perpendicular to the orbital plane. In addition, dee electrodes 31 and 32 which excite a radiofrequency electric field, an extraction septum magnet 40, a kicker magnetic field generating coil 50, and a magnetic field distribution adjusting coil 60 are provided. As will be described later, a kicker magnetic field adopts a massless septum method in which a magnetic field is fed only to a specific position in the radial direction of the accelerator. The kicker magnetic field is excited by passing a current through a pair of coils installed plane-symmetrically in a direction perpendicular to the beam orbital plane. The beam is injected to the accelerator 1 from an injection point 120 in a state of low energy ions. The injected beam is accelerated each time it passes through an electric field gap by the radiofrequency electric field excited by the radiofrequency cavity. The accelerator 1 defines a main magnetic field distribution such that the orbital center of the beam moves in one direction on the same plane in accordance with the acceleration of the beam. Further, a shape of the magnetic pole and coil arrangement are plane-symmetrical with respect to the central plane such that an in-plane component becomes 0 at the central plane. As a result of the distribution of the main magnetic field being bilaterally symmetrical with respect to the axis AA' in the central plane, the shapes of the magnetic pole 15 and the dee electrodes 31 and 32 are bilaterally symmetrical. A trim coil 60 for fine adjustment of the magnetic field is provided on the magnetic pole 15, and a trim coil current is adjusted before operation so as to ensure stability of the betatron oscillation.

Figure 3:
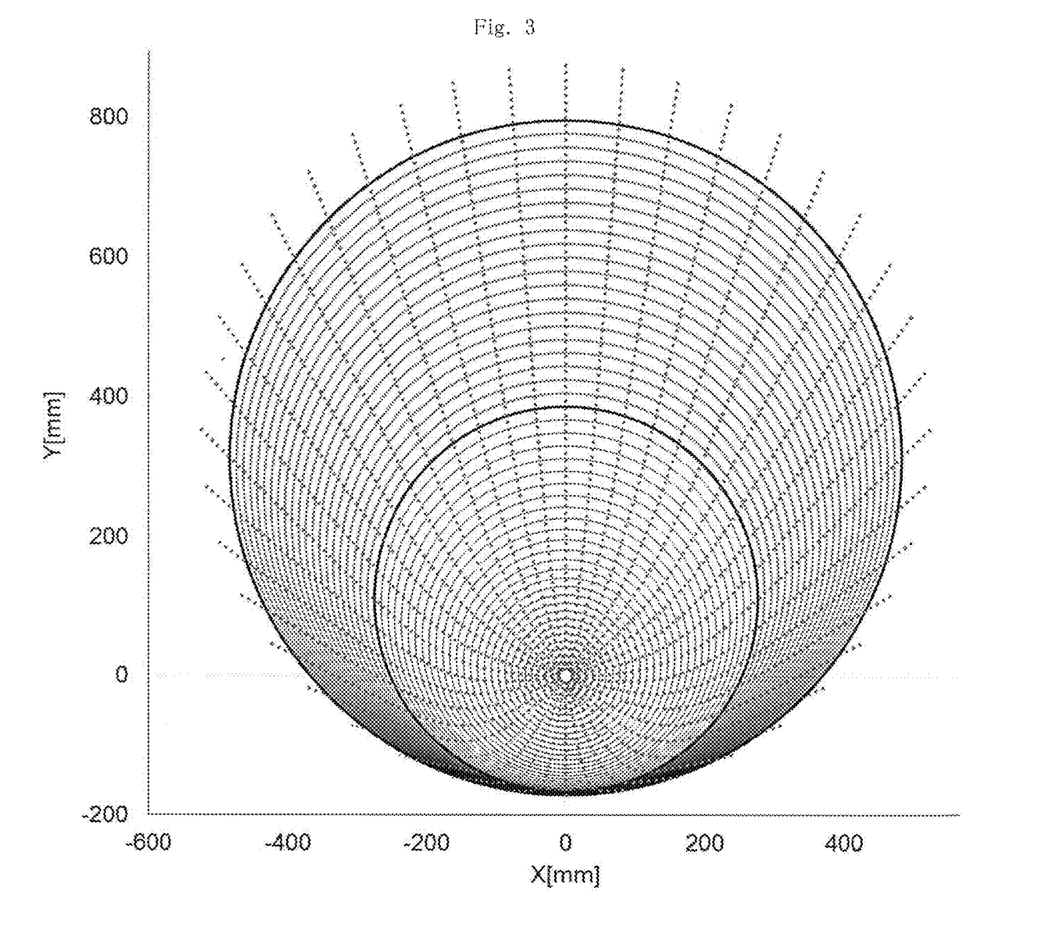
FIG. 3 is a design orbit shape of the accelerator 1 in the embodiment.

Next, an orbit of a beam circulating in the accelerator will be described. The orbit of each energy is illustrated in FIG. 3. The closed orbit indicates the orbit of 50 energy species by solid lines at every 0.04 Tm of magnetic stiffness rate from a maximum energy of 235 MeV. Dotted lines are lines connecting a same circulating phase of each orbit, and are referred to as an equal circulating phase line. Equal circulating phase lines are plotted for each circulating phase π/20 from an aggregation region. An acceleration gap formed between opposing grounded electrodes 35 and the radiofrequency cavities 31 and 32 is provided along the equal circulating phase line. In a low energy region of 4 MeV or less, the orbit is centered near an injection point of ions which is the same as in the cyclotron. However, the orbit of energy greater than 100 MeV is densely gathered near an injection point of an extraction septum magnet. On the contrary, in a region where the massless septum 50 is installed, the orbits are in a positional relationship separated from each other. A point where the orbit is densely gathered is referred to as an aggregation region, and a discrete region is referred to as a discrete region. In the discrete region, the beam spreads in accordance with the energy in a wide region in the central plane, and the beam of the energy corresponding to an excitation position is kicked by properly determining the excitation position of the magnetic field by the massless septum. The beam deviated from the predetermined design orbit by the kick is injected on a septum magnet installed in the aggregation region on a downstream side of a half circumference. The septum magnet gives the beam the bend required to place the extraction beam onto the defined design orbit on the extraction path 140. Specifically, in FIG. 2, a magnetic field in a direction to strengthen a main magnetic field is excited in a coil installed on the right side, a magnetic field in a direction to cancel out the main magnetic field is excited on the left side, and a beam is guided to the extraction path 140.

In order to generate the orbital configuration as described above and stable oscillation around the orbit, in the accelerator 1 in the embodiment, the main magnetic field distribution in which a value of the magnetic field decreases toward the outer side of the bending radial direction of the design orbit is used. Further, the magnetic field is fixed along the design orbit. Thus, the design orbit is circular, and the orbital radius and circulating time increase as the beam energy increases.

The design orbit will be described in detail based on a Formula (1).

Formula 1

$$n = -\frac{\rho}{|B|}\frac{\partial B}{\partial r} \quad (1)$$

Here, ρ represents a bending radius of a design orbit, B represents a magnetic field strength, and δB/δr represents a magnetic field gradient in a radial direction.

When a normalized magnetic field gradient n defined by Formula (1) is greater than 0 and less than 1, the particles slightly deviated from the design orbit in the radial direction receive a restoring force returning to the design orbit, and at the same time, the particles deviated in a direction perpendicular to the orbital plane also receive the restoring force from the main magnetic field in a direction to return to the orbital plane. That is, if the magnetic field is appropriately reduced with respect to the energy of the beam, the particles that are always deviated from the design orbit will have restoring force acting in a direction to return to the design orbit, and will oscillate in a vicinity of the design orbit. As a result, it is possible to stably circulate and accelerate the beam. Oscillation centered on this design orbit is referred to as a betatron oscillation.

The main magnetic field distribution described above is excited by magnetizing the magnetic pole 15 by passing a predetermined excitation current through the main coil 13. In order to form a distribution in which the magnetic field is increased at the ion injection point and the magnetic field is reduced toward an outer periphery, a distance (gap) opposed to the magnetic pole 15 is the smallest at the injection point, and becomes larger toward the outer periphery. Further, a shape of the magnetic pole is plane-symmetrical with respect to a plane (orbital plane) passing through a gap center, and has only a magnetic field component in a direction perpendicular to the orbital plane on the orbital plane. Further, fine adjustment of the magnetic field distribution is performed by adjusting the current fed to the trim coil 20 installed on a magnetic pole plane to excite the predetermined magnetic field distribution.

The radiofrequency cavity excites the electric field in the acceleration gap by a λ/4 resonant mode. A radiofrequency power is introduced from an external radiofrequency power supply through a coupler 211. The radiofrequency cavity is connected to the dee electrodes 31 and 32 inserted into the gap, and the radiofrequency electric field is excited between the dee electrodes 31 and 32 and the grounded electrodes 35. In the accelerator of the invention, in order to excite the radiofrequency electric field in synchronization with the circulating of the beam, the frequency of the electric field is modulated in accordance with the energy of the circulating beam. In the cavity using the resonance mode as used in the invention, it is necessary to sweep the frequency of the radiofrequency in a range wider than the width of the resonance. Therefore, it is necessary to change the resonance frequency of the cavity. This control is performed by changing electrostatic capacity of the rotating variable capacitance capacitor 212 installed at the end of the cavity. The rotating variable capacitance capacitor 212 controls the electrostatic capacitance generated between a conductor plate and an outer conductor directly connected to a rotating shaft by a rotating angle of the rotating shaft 213. That is, the rotating angle of the rotating shaft 213 is changed along with the acceleration of the beam.

In order to extract a predetermined extraction beam at target energy, any one or a plurality of coils of the massless septum coils 50 are selected based on the target energy and a predetermined excitation current is passed. When the current is not passed through the massless septum coil 50, the beam of the target energy circulates along the design orbit. However, when the current is passed through the massless septum coil 50, the beam reaching the target energy is deviated from the orbit by the kick magnetic field caused by the massless septum coil 50. As described above, the beam deviated from the orbit stably oscillates around the design orbit. That is, the betatron oscillation in the orbital plane is excited by the massless septum coil 50. When a position of the kick by the massless septum coil 50 and a position of the aggregation point are in an appropriate positional relationship, it is possible to displace the beam toward the outer side of the radial direction at the aggregation point by the kick by the massless septum coil 50.

A behavior of the beam from the injection to the extraction of the beam of the accelerator will be described. The operation of the accelerator includes three steps of injection, acceleration, and extraction.

In the injection step, a beam of low energy is output from the ion source 12 arranged at a position different in the radial direction from the center of gravity of the annular coil 13, and the beam is guided to the beam passing region through the injection point 120 located in an injection portion 121 which is an inner region of the innermost closed orbit. After going through an accumulation process to be described later, the beam injected on the beam passing region 20 is accelerated by the radiofrequency electric field whose energy is increased and a wobbling radius of the orbit is increased.

After that, the beam is accelerated while ensuring traveling direction stability by the radiofrequency electric field. That is, instead of passing through the acceleration gap at the time when the radiofrequency electric field becomes maximum, the beam passes through the acceleration gap when the radiofrequency electric field is reduced temporally. Then, since the frequency of the radiofrequency electric field and the circulating frequency of the beam are synchronized at a ratio which is exactly an integer multiple, the particles accelerated in the phase of the predetermined acceleration electric field are accelerated in the same phase as the next turn. Meanwhile, since the particles accelerated with a phase earlier than an acceleration phase are larger in acceleration amount than the particles accelerated by the acceleration phase, the particles are accelerated with a delayed phase in the next turn. On the contrary, since the particles accelerated with a phase slower than the acceleration phase may be smaller in acceleration amount than the particles accelerated by the acceleration phase, the particles are accelerated with an advanced phase in the next turn. As described above, the particles at the timing deviated from the predetermined acceleration phase move in the direction of returning to the acceleration phase, and this action makes it possible to stably oscillate even in a phase plane (traveling direction) composed of momentum and the phase. This oscillation is referred to as synchrotron oscillation. That is, the particles during acceleration are gradually accelerated while performing the synchrotron oscillation, and reach the predetermined energy to be extracted.

The beam that has reached the predetermined energy receives an action of a kick magnetic field caused by the massless septum coil, rides on an extraction channel, which is the beam extraction path 140 formed by the extraction septum magnet from the aggregation point, and is extracted from the accelerator.

Figure 4:
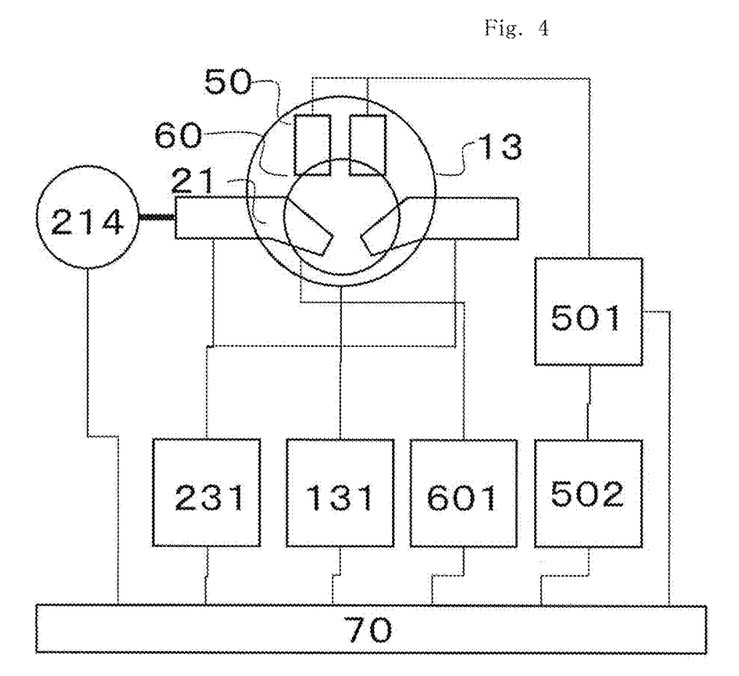
FIG. 4 is a system configuration diagram of the accelerator 1 in the embodiment.

Operation flow for realizing this operation will be described with reference to FIG. 4. FIG. 4 is a block diagram of the accelerator. A main coil 13 is connected to a main coil power supply 131; the massless septum coil 50 is connected to a massless septum coil power supply 502 via a switch 501; the trim coil 60 is connected to a trim coil power supply 601; and radiofrequency cavities 21, 22 are connected to a radiofrequency source 231. The switch 501 has a function of selectively causing a current to pass among a plurality of massless septum coils present. Each switch and power supply is connected to a control system 70, and a connection destination, the output current, and the frequency of output radiofrequency are controlled. Further, a servo motor 214 is connected to the rotating shaft 213 of the rotating variable capacitance capacitor 212 of the radiofrequency cavity 21, and is controlled to a predetermined rotating angle by an instruction from the control system 70 while receiving feedback from an angle sensor.

An operator first inputs a target value of the extraction beam to the control system 70. The control system 70 calculates massless septum coils through which the current passes and a massless septum coil current value based on a value of the input energy. Then, the switch 501 is controlled so as to connect the predetermined massless septum coil 50 and the massless septum coil power supply 502. Next, an output of the power supply 502 is controlled so as to cause the calculated excitation current to pass through the massless septum coils. Next, the rotating angle of the rotating shaft 213 is adjusted to a value corresponding to the time of injection. At this time, the resonance frequency of the radiofrequency cavity 21 is in a highest state during the operation period, and the frequency of the radiofrequency output from the radiofrequency source 231 is also in a highest state accordingly.

In this state, since preparation for injection of the beam is completed, the beam is extracted from the ion source and the ions are introduced into the beam passing region 20 through the injection portion 121. In order to increase the amount of beam to be accelerated, the frequency of the radiofrequency output from the radiofrequency source 231 and the rotating angle of the rotating shaft 213 are kept fixed by about 10 turns as the circulating time of the beam. Then, when a predetermined time elapses, beams are accumulated in the traveling direction phase space, and become beams having a wide phase width and a momentum width. Subsequently, the process proceeds to the acceleration step, in which the frequency of the radiofrequency output from the radiofrequency source 231 and the resonance frequency of the radiofrequency cavity 21 are synchronously lowered gradually. Then, the particles performing the synchrotron oscillation described above synchrotron oscillate around the acceleration phase defined by a changing rate of the frequency of the radiofrequency, and are gradually accelerated. Then, the particles is accelerated to the extracted target energy and extracted. When all beams circulating in the beam passing region are extracted, the frequency of the radiofrequency output again from the radiofrequency source 213 and the resonance frequency of the radiofrequency cavity 21 are reset to a value at the time of injection to return to a state where the beam can be injected. This operation can be repeated to extract a desired amount of the beam of the predetermined energy.

Next, when extracting a beam of other energy, the control system 70 calculates an excitation current amount of the massless septum coil and coils through which the current passes from the energy of the extraction beam input to the control system, and controls the switch 501 and the output current of the massless septum coil power supply 50 accordingly. Then, it is confirmed that the magnetic field is excited, and the injection process described above is started. The beam of any energy in the extractable range can be extracted in any order by repeating this procedure.

Figure 5:
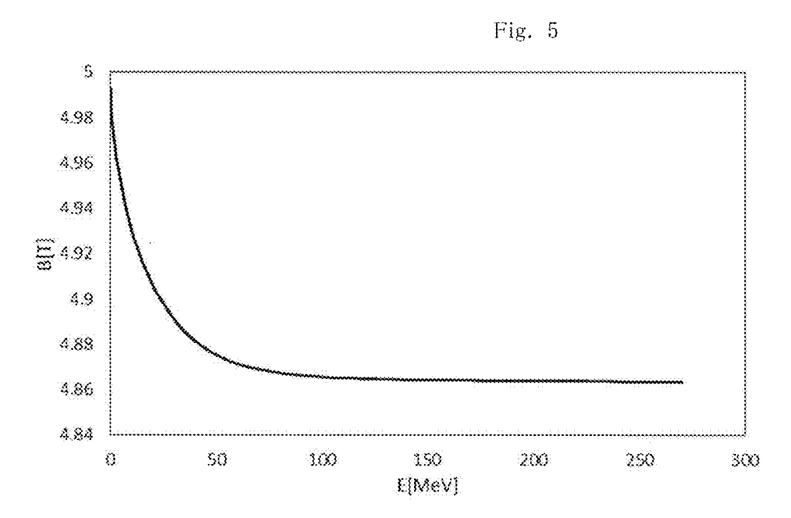
FIG. 5 is energy dependence of a main magnetic field of the accelerator 1 in the embodiment.

Here, the main magnetic field distribution excited in the beam passing region 20 will be described. The main magnetic field is a uniform magnetic field along the orbit of each energy, and a value of the magnetic field can be expressed as a function of the beam energy. The relationship between the energy and the main magnetic field in the embodiment is shown in FIG. 5. The magnetic field near the injection point 120 is the highest, which is 5 T. In addition, at 235 MeV which is the maximum extractable energy, the magnetic field is 4.86 T. In this case, a magnetic field gradient in the radial direction of the beam orbit at the aggregation point is 0.8 T/m. In this case, a normalized gradient in Formula (1) is 0 or more and 1 or less at all points on the orbit, and the stability of the betatron oscillation can be ensured. Here, the magnetic field is formed such that the magnetic field gradient decreases with the increase in energy on an inner periphery formed around the injection point, and the magnetic field is formed such that the magnetic field gradient is substantially linear in an outer peripheral region where the beam orbits are aggregated on one side, thereby enabling stable circulation.

Figure 6:
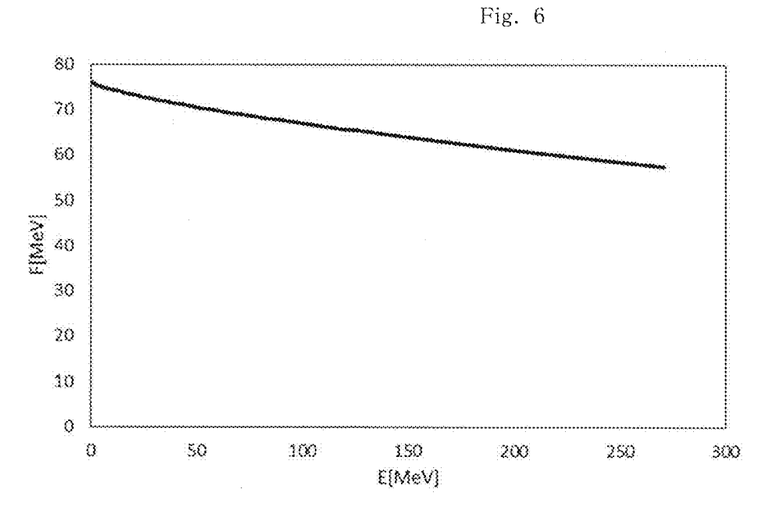
FIG. 6 is energy dependence of circulating frequency of the accelerator 1 in the embodiment.

Further, in the accelerator, as described above, the circulating frequency of the beam decreases along with the acceleration. The dependence of the circulating frequency is shown in FIG. 6. Since the circulating frequency of the beam is modulated in a range of 59 to 76 MHz, the frequency of the radiofrequency is modulated in synchronization therewith. Here, a radiofrequency feeding control is performed such that the frequency gradient decreases with the increase in energy on the inner periphery formed around the injection point of the beam orbit, and the radiofrequency feeding control is performed such that the frequency gradient is substantially linear in the outer peripheral region where the beam orbits are aggregated on one side, thereby enabling stable circulation.

According to the above configuration and operation procedure, a miniaturized accelerator capable of varying the energy of the beam to be extracted is realized.

To summarize, in the embodiment, the magnetic field is decreased with respect to the bending radial direction of the beam orbit. Further, the orbit circulating along with acceleration is displaced in one direction, and a region (aggregation point) in which each orbit having different energy densely aggregates and a region (discrete region) in which each orbit having different energy is sparsely discrete are formed. In this case, since the isochronous property is lost, it is necessary to change the frequency of the radiofrequency electric field to be excited in order to accelerate the beam in synchronization with the acceleration of the beam, and the beam becomes pulsed. Then, it is possible to extract the kicked beam by exciting the kick magnetic field around the orbit of a specific energy by a plurality of coils installed in the discrete region; and it is possible to extract a plurality of types of energy by selectively controlling a position at which the kick magnetic field is excited. That is, variable energy property can be ensured. Further, in the case of an accelerator using the present technique, the magnetic field distribution is simple compared to a related cyclotron or a variable energy accelerator, which facilitates miniaturization.

Embodiment 2

Figure 8:
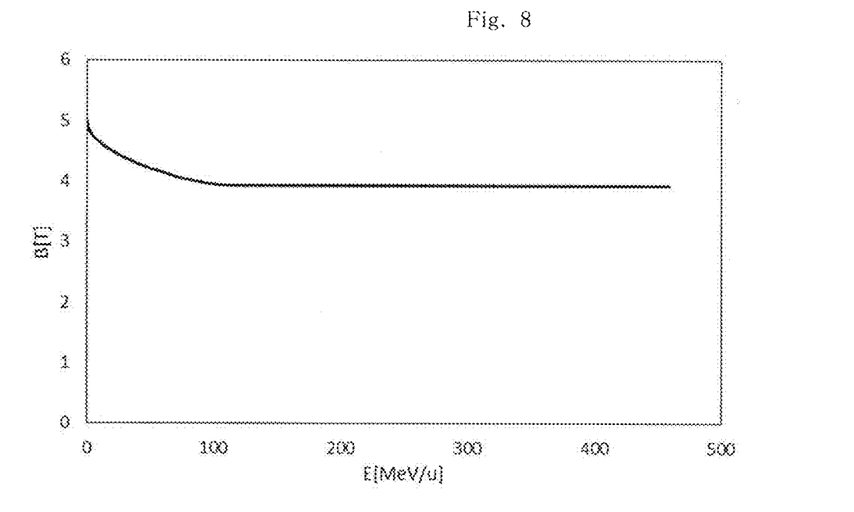
FIG. 8 is energy dependence of a main magnetic field of the accelerator 2 in the embodiment.
Figure 9:
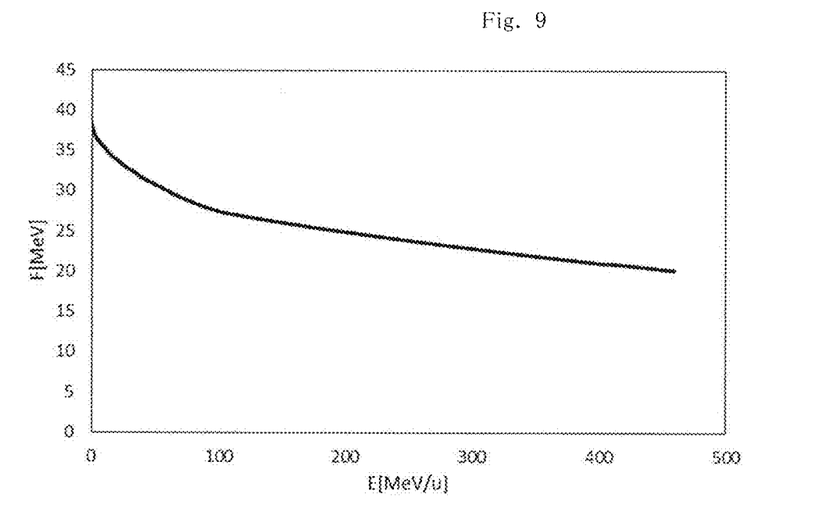
FIG. 9 is energy dependence of the circulating frequency of the accelerator 2 in the embodiment.

In the second embodiment, acceleration nuclide is a carbon ion in the first embodiment. The accelerator is a frequency modulation variable energy accelerator capable of extracting carbon ions in a range of kinetic energy of 140 MeV to 430 MeV per nucleus. Operation principle, machine configuration, and operating procedure are the same as in the first embodiment, and thus will be omitted. The difference lies in a relationship of the size of the orbital radius and the magnetic field and the energy and a relationship between the circulating frequency and the energy. Therefore, the relationships thereof are shown in FIGS. 7 to 9.

Figure 7:
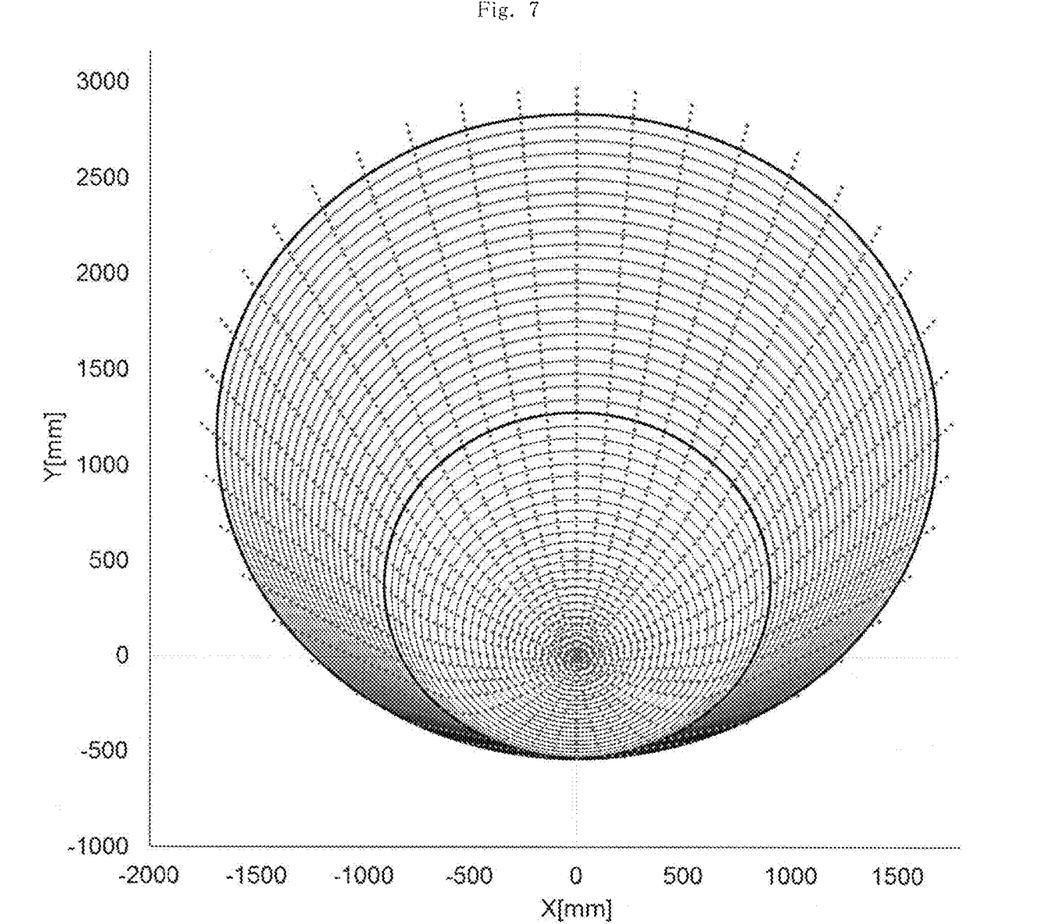
FIG. 7 is a design orbit shape of an accelerator 2 in an embodiment.

An orbit of each energy of the beam circulating in the accelerator is shown in FIG. 7. FIG. 8 shows a relationship between the energy and the main magnetic field in the embodiment. In this case, the magnetic field gradient in the radial direction of the beam orbit at the aggregation point is 2 T/m. In this case, a normalized gradient in Formula (1) is 0 or more and 1 or less at all points on the orbit, and the stability of the betatron oscillation can be ensured. Further, FIG. 9 shows the dependency of the circulating frequency in the embodiment. In the accelerator, as described above, the circulating frequency of the beam decreases along with the acceleration. Since the circulating frequency of the beam is modulated in a range of 20 to 39 MHz, the frequency of the radiofrequency is modulated in synchronization therewith. According to the above configuration and operation procedure, a miniaturized accelerator capable of varying the energy of the beam to be extracted is realized.

Embodiment 3

Figure 10:
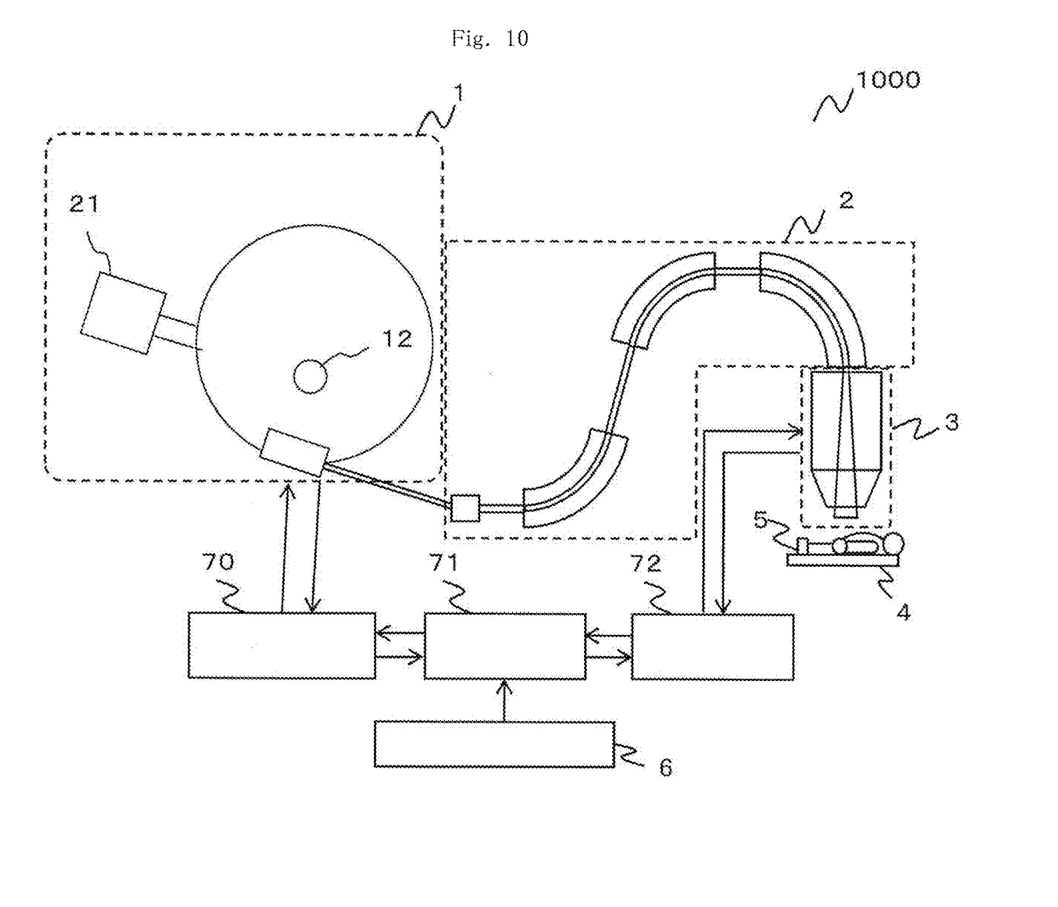
FIG. 10 is an overall outline of the particle therapy system in an embodiment.

A third embodiment is a particle therapy system 1000 using the accelerator 1 described in the first and second embodiments. FIG. 10 illustrates an overall outline of the particle therapy system. The particle therapy system includes an accelerator 1, a transfer 2 which transfers an accelerated ion beam, an irradiation system 3 which irradiates the transferred beam, a positioning system 4 which holds a target irradiated with the beam, control systems 71 and 72, and a treatment planning system 6. The particle therapy system irradiates a patient with an appropriate value of the energy of a proton beam or a carbon beam (hereinafter, collectively referred to as particle beam) irradiated by a depth from a body surface of a target volume of a patient 5 placed on the positioning system 4. The energy of the particle beam to be irradiated is determined by the treatment planning created by the treatment planning system 6. However, the particle therapy system can be realized by the procedure in which the energy and irradiation dose of the particle beam determined by the treatment planning are sequentially input to the control system 70 via an overall control system 71, coordinated with the irradiation control system 72 which controls the irradiation system 3, and moved to the next energy at the time of irradiation with an appropriate dose to irradiate the particle beam again.

In this case, an energy changing system that is smaller than the related accelerator and installed in a transport, which is necessary in a cyclotron or the like, becomes unnecessary, and the miniaturization and cost reduction of the whole system can be achieved.

REFERENCE SIGN LIST

1 accelerator
11 magnet
12 ion source
13 main coil
14 return yoke
15 magnetic pole
20 beam passing region
21 radiofrequency cavity
31-32 dee electrode
40 extraction septum magnet
50 massless septum coil
60 trim coil
70 control system
71 overall control system
72 irradiation control system
111 extraction beam through hole
112-113 coil connection through hole
114 radiofrequency input through hole
115 beam injection through hole
120 injection point
131 main coil power supply
140 beam extraction path
211 input coupler
212 rotating variable capacitance capacitor
213 rotating shaft
214 servo motor
231 radiofrequency source
501 switch
502 massless septum power supply
601 trim coil power supply
1000 particle therapy system

The invention claimed is:

1. An accelerator, comprising:
a pair of magnets forming a magnetic field therebetween;
an ion source which injects ions between the pair of magnets;
an acceleration electrode which accelerates the ions; and
a beam extraction path which extracts the ions to an outside, wherein
a plurality of ring-shaped beam closed orbits formed by the pair of magnets, in which ions of different energies respectively circulate, are aggregated on one side; and
the magnetic field formed by the pair of magnets is uniform along the plurality of ring-shaped beam closed orbits and decreases as energy increases.
2. The accelerator according to claim 1, wherein
a distance between magnetic poles formed respectively in the pair of magnets is smallest in a vicinity of an injection point and increases toward an outer periphery.
3. The accelerator according to claim 1, wherein
the plurality of ring-shaped beam closed orbits aggregate on one side in a predetermined energy range.
4. The accelerator according to claim 1, wherein
the beam closed orbit is formed such that the plurality of ring-shaped beam closed orbits aggregate on one side in a predetermined outer peripheral region and do not aggregate in a predetermined inner peripheral region; and
the pair of magnets form the magnetic field such that a magnetic field gradient is substantially linear in the predetermined outer peripheral region where the plurality of ring-shaped beam closed orbits are aggregated on one side.
5. A particle therapy system, comprising:
the accelerator according to claim 1;
a transfer which transfers ions accelerated by the accelerator;
an irradiation system which irradiates a target with the ions transferred by the transfer;
a positioning system which supports the target; and
a treatment planning creation system which creates a plan of performing the irradiation.

* * * * *